(12) United States Patent
Mihalik (10) Patent No.: US 9,345,529 B2
(45) Date of Patent: May 24, 2016

(54) MAPPING WIRE WITH HEATING ELEMENT TO ALLOW AXIAL MOVEMENT DURING CRYOBALLOON ABLATION

(71) Applicant: MEDTRONIC CRYOCATH LP, Toronto (CA)

(72) Inventor: Teresa Ann Mihalik, Montreal (CA)

(73) Assignee: Medtronic CryoCath LP, Toronto, Ontario (CA)

( * ) Notice: Subject to any disclaimer, the term of this patent is extended or adjusted under 35 U.S.C. 154(b) by 221 days.

(21) Appl. No.: 13/941,819

(22) Filed: Jul. 15, 2013

(65) Prior Publication Data

US 2015/0018808 A1    Jan. 15, 2015

(51) Int. Cl.
*A61B 18/02* (2006.01)
*A61B 18/00* (2006.01)
*A61B 19/00* (2006.01)

(52) U.S. Cl.
CPC ....... *A61B 18/02* (2013.01); *A61B 2018/00041* (2013.01); *A61B 2018/00375* (2013.01); *A61B 2018/00577* (2013.01); *A61B 2018/00791* (2013.01); *A61B 2018/00839* (2013.01); *A61B 2018/0212* (2013.01); *A61B 2019/464* (2013.01)

(58) Field of Classification Search
CPC ........... A61B 18/02; A61B 2018/0212; A61B 2018/0022; A61B 2018/00404; A61B 2018/00214; A61B 2018/00351; A61B 2018/00262; A61B 2018/00642; A61B 2018/00375; A61B 2018/00011; A61B 2018/00797; A61B 17/8897; A61B 2017/00469; A61B 2017/22038; A61B 2017/22042; A61B 2017/22047; A61B 2017/22048
USPC ...................................... 606/20–26
See application file for complete search history.

(56) References Cited

U.S. PATENT DOCUMENTS

| 5,423,807 | A | 6/1995 | Milder |
| 6,939,338 | B2 | 9/2005 | Waldhauser et al. |
| 7,255,693 | B1 | 8/2007 | Johnston et al. |
| 2003/0176810 | A1 | 9/2003 | Maahs et al. |
| 2006/0135953 | A1* | 6/2006 | Kania et al. ..................... 606/21 |
| 2007/0276360 | A1* | 11/2007 | Johnston et al. ................ 606/21 |
| 2011/0184274 | A1 | 7/2011 | Rosenberg et al. |
| 2012/0150107 | A1* | 6/2012 | Cheung et al. ............. 604/96.01 |

FOREIGN PATENT DOCUMENTS

WO    0141664 A1    6/2001

OTHER PUBLICATIONS

International Search Report and Written Opinion dated Jul. 22, 2014 for International Application Serial No. PCT/CA2014/000497, International Filing Date: Jun. 12, 2014 consisting of 7 pages.

* cited by examiner

*Primary Examiner* — Michael Peffley
*Assistant Examiner* — Khadijeh Vahdat
(74) *Attorney, Agent, or Firm* — Christopher & Weisberg, P.A.

(57) ABSTRACT

A method and system for cryotreatment of target tissue using a cryotreatment catheter through which a mapping catheter may be freely movable, even during activation of the cryotreatment element. The cryotreatment system may include a cryotreatment catheter, a mapping catheter slidably disposed within a lumen of the cryotreatment catheter, and one or more heating elements. The one or more heating elements may be disposed on the mapping catheter or within the lumen of the cryotreatment catheter. Activation of the one or more heating elements prevents the freezing of, or thaws, fluid within the lumen of the cryotreatment device when one or more cryotreatment elements are activated. The lack of frozen fluid within the lumen allows the mapping catheter to freely move within the cryotreatment catheter during a cryotreatment procedure, so that the mapping catheter may be positioned proximate the treatment site after initiation of cryotreatment.

9 Claims, 7 Drawing Sheets

MAPPING WIRE WITH HEATING ELEMENT TO ALLOW AXIAL MOVEMENT DURING CRYOBALLOON ABLATION

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates to a method and system for a heatable mapping cryotreatment catheter that allows for axial movement of the mapping cryotreatment catheter through a lumen of a medical cryotreatment catheter during a cryoablation procedure.

BACKGROUND OF THE INVENTION

A cardiac arrhythmia is a condition in which the heart's normal rhythm is disrupted. There are many types of cardiac arrhythmias, including supraventricular arrhythmias that begin above the ventricles (such as premature atrial contractions, atrial flutter, accessory pathway tachycardias, atrial fibrillation, and AV nodal reentrant tachycardia), ventricular arrhythmias that begin in the lower chambers of the heart (such as premature ventricular contractions, ventricular tachycardia, ventricular fibrillation, and long QT syndrome), and bradyarrhythmias that involve slow heart rhythms and may arise from disease in the heart's conduction system.

Certain types of cardiac arrhythmias, including ventricular tachycardia and atrial fibrillation, may be treated by ablation (for example, radiofrequency (RF) ablation, cryoablation, ultrasound ablation, laser ablation, microwave ablation, and the like), either endocardially or epicardially. For example, atrial fibrillation (AF) is frequently treated with pulmonary vein ablation (also called pulmonary vein antrum isolation, or PVAI), a procedure that may involve inserting a mapping cryotreatment catheter through the left atrium of the patient's heart to the pulmonary vein (PV) ostium to map electrical impulses or potentials at the PV ostium before and/or after cryoablation. There is a depth within the PV at which electrical impulses are absent (such a location may be referred to as being "deep" within the PV), with the strength and/or prevalence of electrical impulses being greater closer to the PV ostium. The mapping catheter then may be inserted into the PV before ablation to act as an anchor to a cryoablation element and to support the cryoablation element during positioning at the left atrium/pulmonary vein (LA-PV) junction. Once the mapping catheter is properly seated within the PV, an ablation element (such as a cryoballoon or other ablation catheter configured to be advanced over a wire) is advanced over the mapping catheter until it is in contact with the ostium of the PV, within the left atrium. Proper contact between the cryoballoon and the PV ostium, which results in PV occlusion, may be confirmed using visualization techniques such as fluoroscopy.

Once the cryoballoon is in good position, the mapping catheter is slowly pulled back from deep within the PV to an area closer to the PV ostium. In this manner, it may be possible to detect and record pulmonary vein potentials (PVPs) with the mapping catheter, which may provide insight as to the time-to-effect during onset of ablation. Although it is desirable to collect this additional data, users are often forced to leave the mapping catheter within the PV during the cryotreatment procedure (for example, cryoablation). This is because, in some cases, retraction of the mapping catheter once the cryoballoon is in place reduces or eliminates the support provided to the cryoballoon by the mapping catheter, and the cryoballoon may slip out of place (that is, occlusion of the PV may be compromised). In those cases, the user must re-advance the mapping catheter back into the vein and reposition the cryoballoon. Further, repositioning the cryoballoon typically involves reassessing PV occlusion, such as by the injection of a contrast medium from the cryoballon lumen (such as a guide wire lumen, within which the mapping catheter is slidably disposed) and imaging by fluoroscopy. The use of contrast medium and fluoroscopy not only exposes the patient and clinicians to radiation, but is sometimes poorly tolerated by some patients, including those with renal insufficiency.

During the cryotreatment procedure (for example, cryoablation), refrigerant circulating through the cryoballoon absorbs heat from surrounding tissue. As the tissue freezes, blood adjacent the treatment site may also freeze, creating an "ice ball" that temporarily adheres the cryoballoon to the tissue at the treatment site, a phenomenon called cryoadhesion. Once cryoadhesion occurs, retraction of the mapping catheter from within the PV has less of an effect on cryoballoon stability and could, in theory, be withdrawn and used to detect and record PVPs proximate the ablation site. However, within about ten seconds from commencement of the cryotreatment procedure, fluids within the guide wire lumen around the mapping catheter freeze, effectively locking the mapping catheter in place and preventing its axial movement. Although some currently known methods may involve retraction of the mapping catheter before the onset of freezing (that is, within the first approximately ten seconds), there are several drawbacks to this method. For example, cryoadhesion between the cryoballoon and the tissue may not yet have occurred, and movement of the mapping catheter without cryoadhesion will unseat the cryoballoon and require repositioning of the cryotreatment device.

It is desirable, therefore, to provide a system that allows for the axial movement of the mapping catheter during all stages of cryotreatment so that the mapping catheter may not only map LA-PV tissue before and after cryotreatment and anchor the cryoballoon against the PV ostium, but also allow for mapping of the PV tissue proximate the PV ostium during cryotreatment as well.

SUMMARY OF THE INVENTION

The present invention advantageously provides a method and system for a cryotreatment catheter through which a mapping catheter may be freely movable, even during activation of the cryotreatment element. In one embodiment, the system may generally include a cryotreatment device including a first elongate body, a guide wire lumen, and a cryotreatment element on the elongate body; a mapping device including a second elongate body, the second elongate body being disposable within the guide wire lumen of the first elongate body; and at least one heating element being within the guide wire lumen proximate the cryotreatment element. The at least one heating element may be on the second elongate body or on a surface of the guide wire lumen. The system may further include a console including a computer having a processor, the processor being in communication with at least one of the cryotreatment device and the mapping device, and at least one temperature sensor disposed within the guide wire lumen, the at least one temperature sensor being in communication with the processor. For example, the processor may be programmable to activate the at least one heating element when the temperature sensor indicates the guide wire lumen has reached a threshold temperature (such as 0° C.). The at least one heating element may include at least two heating elements, with at least one heating element being disposed within the guide wire lumen proximate the cryotreatment element when the mapping device is in a first position within the guide wire lumen, and at least one heating element being disposed within the guide wire lumen proximate the cryotreatment element when the mapping device is in a second position within the guide wire lumen. Due to the heat generated by the at least one heating element, the mapping element may be movable between the first position and the second position during activation of the cryotreatment element. Further, the at least one heating element may be, for example, a band electrode or a thermally conductive wire wound about at least a portion of the mapping device elongate body. The system may further include a radiofrequency energy source in electrical communication with the at least one heating element.

In another embodiment, the system may generally include a cryotreatment catheter including: a first elongate body having a longitudinal axis, a lumen disposed within the first elongate body along the longitudinal axis, and a cryoballoon coupled to a distal portion of the first elongate body; and a mapping catheter including: a second elongate body being disposable within the guide wire lumen and movable along the longitudinal axis, and at least two heatable regions on the mapping device elongate body, at least one of the at least two heatable regions being disposed within the lumen proximate the cryotreatment element when the mapping device is extended a first distance beyond the cryotreatment device elongate body, and at least one of the at least two heatable regions being disposed within the lumen proximate the cryotreatment element when the mapping device is extended a second distance beyond the cryotreatment device elongate body. At least one of the at least two heatable regions may be disposed within the lumen proximate the cryoballoon, and may be activated to generate heat during at least a portion of activation of the cryoballoon.

The method of performing a cryotreatment procedure may generally include positioning a mapping device within a pulmonary vein, positioning a cryoballoon of a cryotreatment device at the pulmonary vein ostium, at least a portion of the mapping device being longitudinally movable within a lumen of the cryotreatment device, activating the cryoballoon to cool adjacent tissue, activating one or more heating elements within the cryotreatment device lumen, and retracting the mapping device a distance within the cryotreatment device while the cryoballoon is activated. For example, the one or more heating elements may be on the mapping device or on a surface of the cryotreatment device lumen. Activation of the one or more heating elements may prevent fluid within the cryotreatment device lumen from freezing while the cryoballoon is activated. Further, at least one heating element may be disposed within the cryotreatment device lumen proximate the cryoballoon when the mapping device is extended, and at least one heating element may be disposed within the cryotreatment device lumen when the mapping device is retracted toward the cryoballoon.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
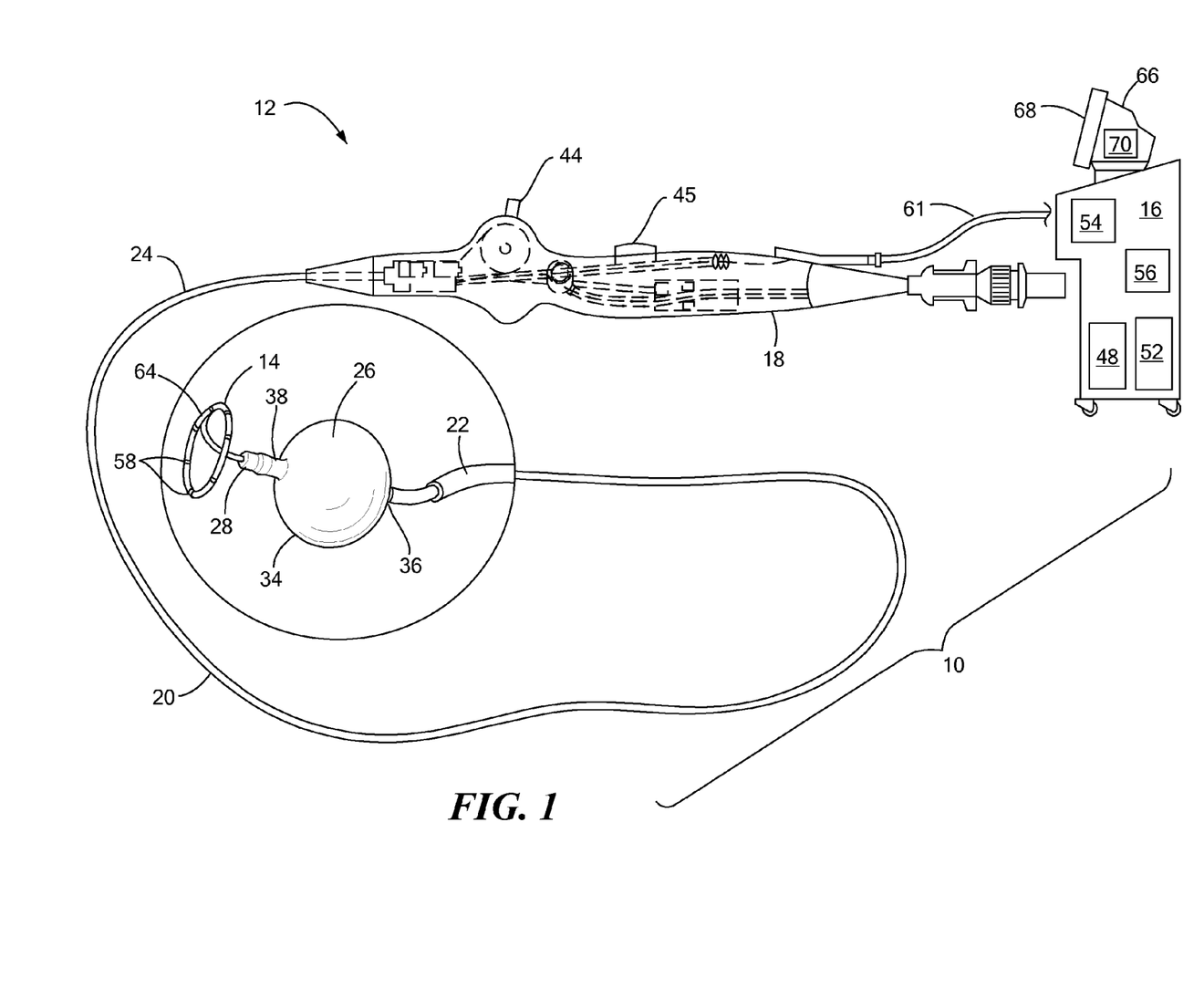
FIG. 1 shows an exemplary system including a cryotreatment catheter and a heatable mapping catheter.

Referring now to FIG. 1, an exemplary system in accordance with the present invention is shown. The system 10 may generally include a cryotreatment catheter 12 for thermally treating an area of tissue, a mapping catheter 14 for sensing and recording electrical signals from tissue (for example, cardiac tissue), and a console 16 that houses various system 10 controls. The system 10 may be adapted for a cryotreatment procedure, such as cryoablation. The system 10 may additionally be adapted for radiofrequency (RF) ablation and/or phased RF ablation, ultrasound ablation, laser ablation, microwave ablation, hot balloon ablation, or other ablation methods or combinations thereof. In any embodiment, however, the cryotreatment catheter 12 will be configured to accept a mapping catheter 14 therethrough. For example, the cryotreatment catheter 12 will include a guide wire lumen or central lumen through which a mapping catheter may be passed, as described in greater detail below.

The cryotreatment catheter 12 may generally include a handle 18, an elongate body 20 having a distal portion 22 and a proximal portion 24, one or more treatment elements 26, a guide wire lumen 28, and one or more sensors 30, 31 (for example, temperature or pressure sensors). Further, the cryotreatment catheter 12 may have a longitudinal axis 32. The treatment element 26 may be a cryoballoon 34, as shown in FIGS. 1-6. The cryoballoon 34 may be coupled to the distal portion 22 of the elongate body 18 of the cryotreatment catheter 12. For example, the cryoballoon 34 may define a proximal portion or neck 36 that is affixed to or coupled to the distal portion 22 of the elongate body 18, and may further define a distal portion or neck 38 that is affixed to or coupled to the guide wire lumen 28 (such as the distal portion 40 of the guide wire lumen 28). The guide wire lumen 28 may lie along the longitudinal axis 28 and be longitudinally movable within the elongate body 18. In this manner, longitudinal movement of the guide wire lumen 28 will affect the shape of the cryoballoon 34, at least when the cryoballoon 34 is inflated. The proximal portion of the guide wire lumen 28 may be in mechanical communication with one or more steering mechanisms 44 in the handle 18 of the cryotreatment catheter 12, such that the guide wire lumen 28 may be longitudinally extended or retracted using one or more steering mechanisms 44, such as knobs, levers, wheels, pull cords, and the like. For example, a longitudinal extender 45 may be included in the handle to advance and retract the mapping catheter 14 within the guide wire lumen 28.

Figure 2:
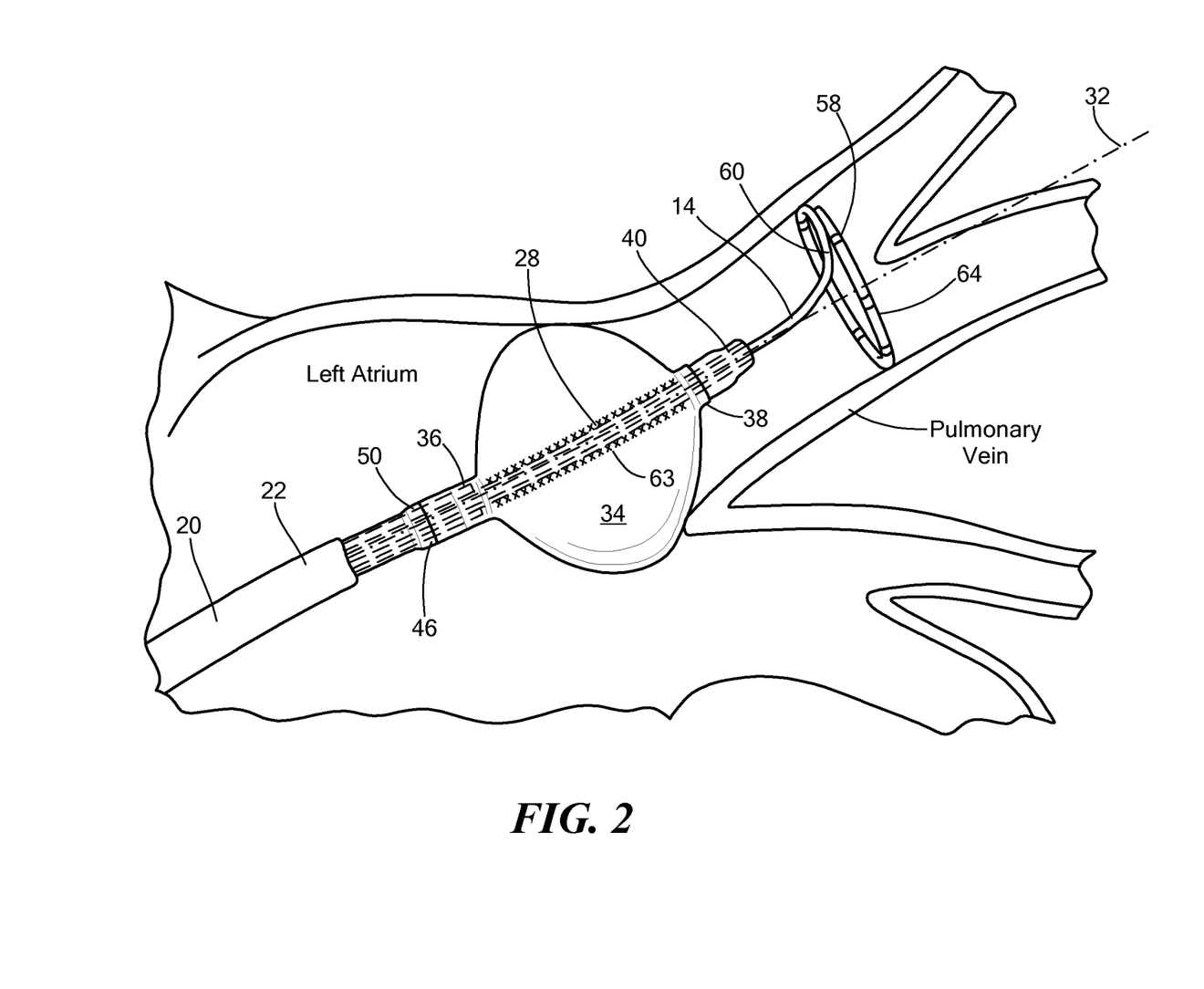
FIG. 2 shows a first view of an exemplary cryotreatment catheter with a heatable mapping catheter, the heatable mapping catheter being extended within the pulmonary vein.
Figure 4:
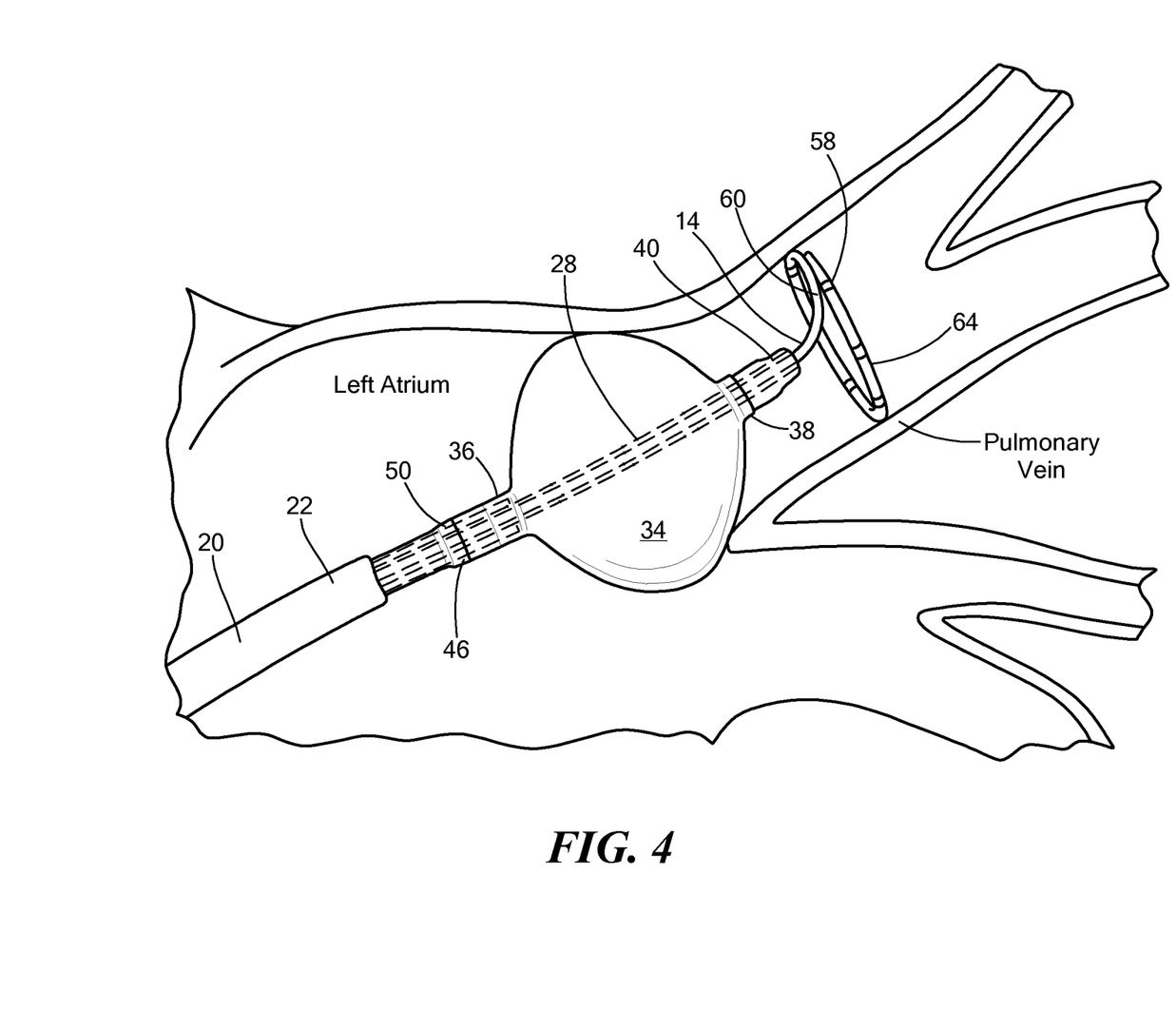
FIG. 4 shows a second view of an exemplary cryotreatment catheter with a heatable mapping catheter, the heatable mapping catheter being retracted proximate the site of cryotreatment.

In addition to the guide wire lumen 28, the cryotreatment catheter 12 may include one or more lumens. As shown in FIGS. 1, 2, and 4, the cryotreatment catheter 12 may include a fluid injection lumen 46 in fluid communication with a fluid supply reservoir 48, and a fluid recovery lumen 50 in fluid communication with a fluid recovery reservoir 52. Further, the fluid recovery lumen 50 may be in communication with a vacuum 54 to facilitate removal of fluid from the cryoballoon 34 (for example, expanded coolant). If the cryotreatment catheter 12 includes thermoelectric cooling elements or electrodes capable of transmitting radiofrequency (RF), ultrasound, microwave, electroporation energy, or the like, the elongate body 18 may include a lumen in electrical communication with an energy generator 56.

The mapping catheter 14 may be passable (longitudinally movable) through the guide wire lumen 28. The mapping catheter 14 may include one or more pairs of mapping elements 58, such as electrodes capable of sensing and recording electrograms from cardiac tissue. The one or more pairs of mapping elements 58 may be disposed along a distal portion 60 of the mapping catheter 14. Further, the one or more pairs of mapping elements 58 may be composed of metal or other electrically conductive material and may be affixed on an outer surface of the mapping catheter 14, integrated and flush with the body of the mapping catheter 14 (such that the mapping catheter has a smooth outer surface), may be areas of exposed electrically conductive material (for example, where an outer insulative layer has been removed), or may be otherwise affixed or coupled to or integrated with the mapping catheter 14.

As is shown and described in more detail in FIGS. 2-5, in one embodiment, the mapping catheter 14 may further include one or more heating elements 62. For example, the one or more heating elements 62 may be located on the mapping catheter 14 such that the one or more heating elements 62 are positioned within the guide wire lumen 28 when the mapping catheter 14 is extended and when it is retracted. The mapping catheter 14 may be in deformable and/or steerable using one or more steering mechanisms 44 into a variety of configurations. For example, the distal portion 60 of the mapping catheter 14 may be deformable into a lasso-type configuration, such that the loop portion 64 and mapping elements 58 may be in contact with at least a portion of an inner circumference of a PV.

The console 16 may be in electrical and fluid communication with the cryotreatment catheter 12 and the mapping catheter 14, and may include one or more fluid (for example, cryotreatment coolant) reservoirs 48, fluid return reservoirs 52, energy generators 56, and computers 66 with displays 68, and may further include various other displays, screens, user input controls, keyboards, buttons, valves, conduits, connectors, power sources, processors, and computers for adjusting and monitoring system 10 parameters. The computer 66 may include one or more processors 70 that are in electrical communication with the one or more pairs of mapping elements 58, the one or more sensors 30, the one or more heating elements 62, and the one or more treatment elements 26 and programmable to execute an algorithm for locating one or more optimal treatment areas, for controlling the temperature of the one or more treatment elements 26, and/or for regulating the operation of the one or more heating elements 62. As a non-limiting embodiment, the proximal portion 61 of the mapping catheter 14 may include an electrical connection that is matable to at least a portion of the console (for example, with the electrophysiology recording equipment) and in electrical communication with the one or more processors 70.

Referring now to FIGS. 2-5, an exemplary cryoablation catheter with a heatable mapping catheter is shown, the heatable mapping catheter being extended within the pulmonary vein. As shown and described in FIG. 1, the mapping catheter 14 may be longitudinally movable within the guide wire lumen 28, so that the mapping catheter 14 may be extended and retracted relative to the cryotreatment catheter 12. For example, the mapping catheter 14 may be extended such that the distal portion 60 is located deep within the PV to anchor the cryotreatment catheter 12 as the cryoballoon 34 is seated at the PV ostium and cryotreatment initiated. When the distal portion 60 of the mapping catheter 14 is positioned deep within the PV, electrical signals from the tissue may not be present, and therefore not recorded by the one or more pairs of mapping elements 58. Before cryotreatment is initiated, the mapping catheter 14 may be partially retracted to a position within the PV that is closer to the PV ostium where electrical signals may be present, such that at least one pair of mapping elements 58 may detect and record PVPs. Further, once the cryoballoon 34 reaches temperatures low enough to cause cryoadhesion between the cryoballoon 34 and the tissue with which the cryoballoon 34 is in contact, the mapping catheter 14 may be further retracted (that is, pulled through the guide wire lumen 28 toward the proximal portion 24 of the elongate body 18) to bring the one or more pairs of mapping elements 58 of the mapping catheter 14 even closer to the cryotreatment site, where electrical signals are stronger and/or more prevalent, for further mapping.

In present systems, when the cryoballoon 34 is cold enough to cause cryoadhesion with adjacent tissue, the cryoballoon 34 is also cold enough to freeze fluids within the guide wire lumen 28, effectively locking the mapping catheter 14 in the extended position. That is, fluids (for example, contrast medium ejected from the guide wire lumen 28 to assess occlusion of the PV ostium by the cryoballoon 34) may freeze within the guide wire lumen 28 and prevent the longitudinal movement of the mapping catheter 14, a phenomenon that usually occurs after approximately 10 seconds from the onset of a cryotreatment procedure, such as cryoablation. In contrast, the one or more heating elements 62 on the mapping catheter 14 may be activated to heat the fluid within the guide wire lumen 28 to a temperature sufficient to melt the frozen fluid or prevent the fluid from freezing, so that the mapping catheter 14 may freely move within the guide wire lumen 28 during all stages of cryotreatment.

A second benefit of having unfrozen fluids within the guide wire lumen 28 is that occlusion assessment of the cryoballoon using the pressure wedge monitoring technique may continue to provide information to the user during the onset of ablation. The pressure wedge monitoring technique is a way to evaluate occlusion without requiring exposure to radiation for the patient and staff. It may be especially useful for patients with renal insufficiency and patients who do not tolerate contrast media. In present systems, fluids within the guide wire lumen 28 freeze within about 10 seconds from the onset of cryotreatment, and pressure readings disappear. This is because the pressure wedge monitoring technique requires the presence of a column of fluid within the cryotreatment device. When the liquid is frozen, the pressure cannot be determined using this method. Thus, there is no information about any loss of position of the cryoballoon 34 unless another technique is used to monitor occlusion. However, fluoroscopy is also nearly impossible to use for assessing cryoballoon 34 position, because the contrast medium cannot be ejected from the cryotreatment catheter 12 through the frozen liquid within the guide wire lumen 28. A technique such as Doppler flow using intravascular ultrasound could be used to assess cryoballoon 34 position; however, such systems are costly and do not always produce satisfactory results.

Figure 3:
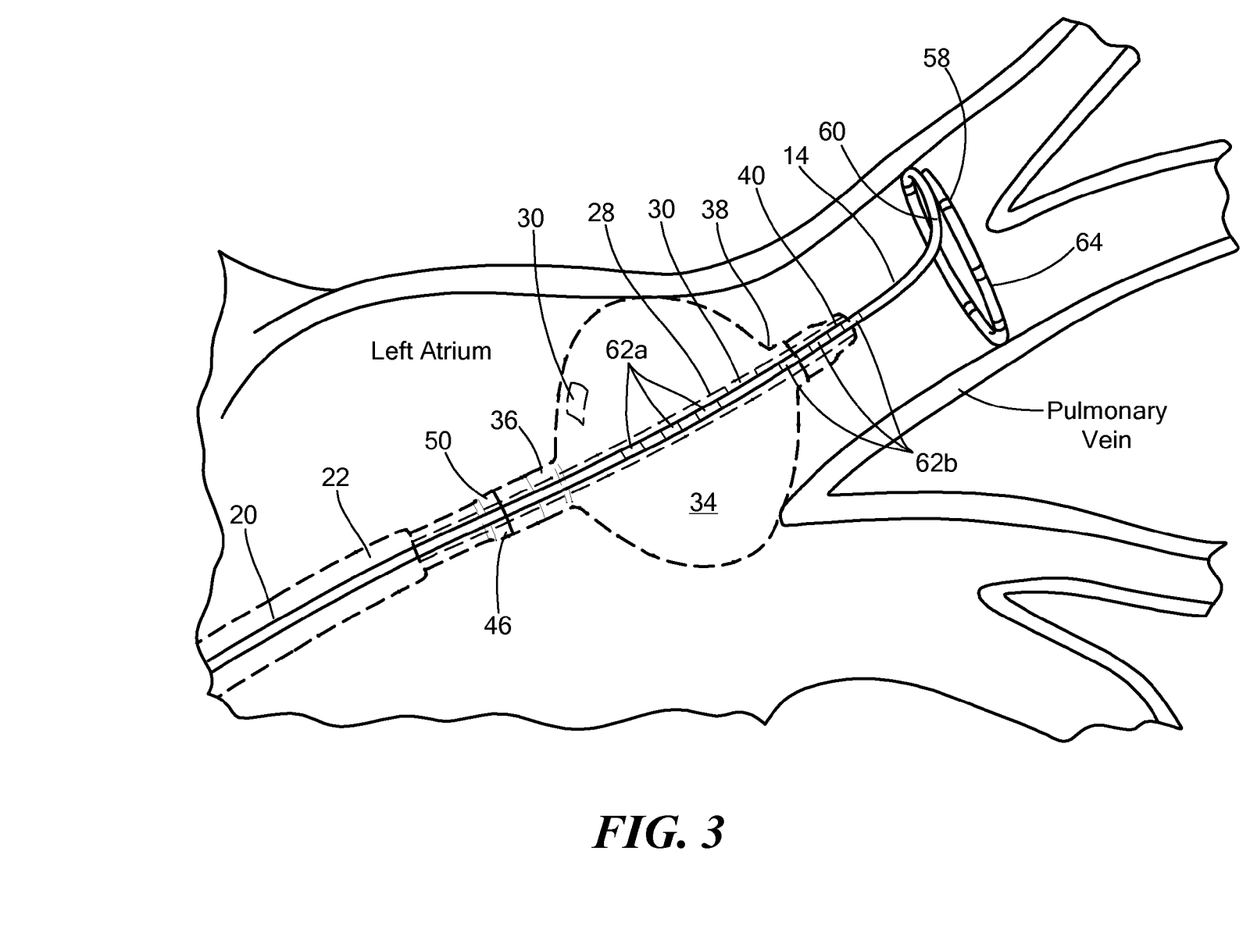
FIG. 3 shows an alternate view of the heatable mapping catheter within the exemplary cryotreatment catheter in the configuration of FIG. 2.
Figure 5:
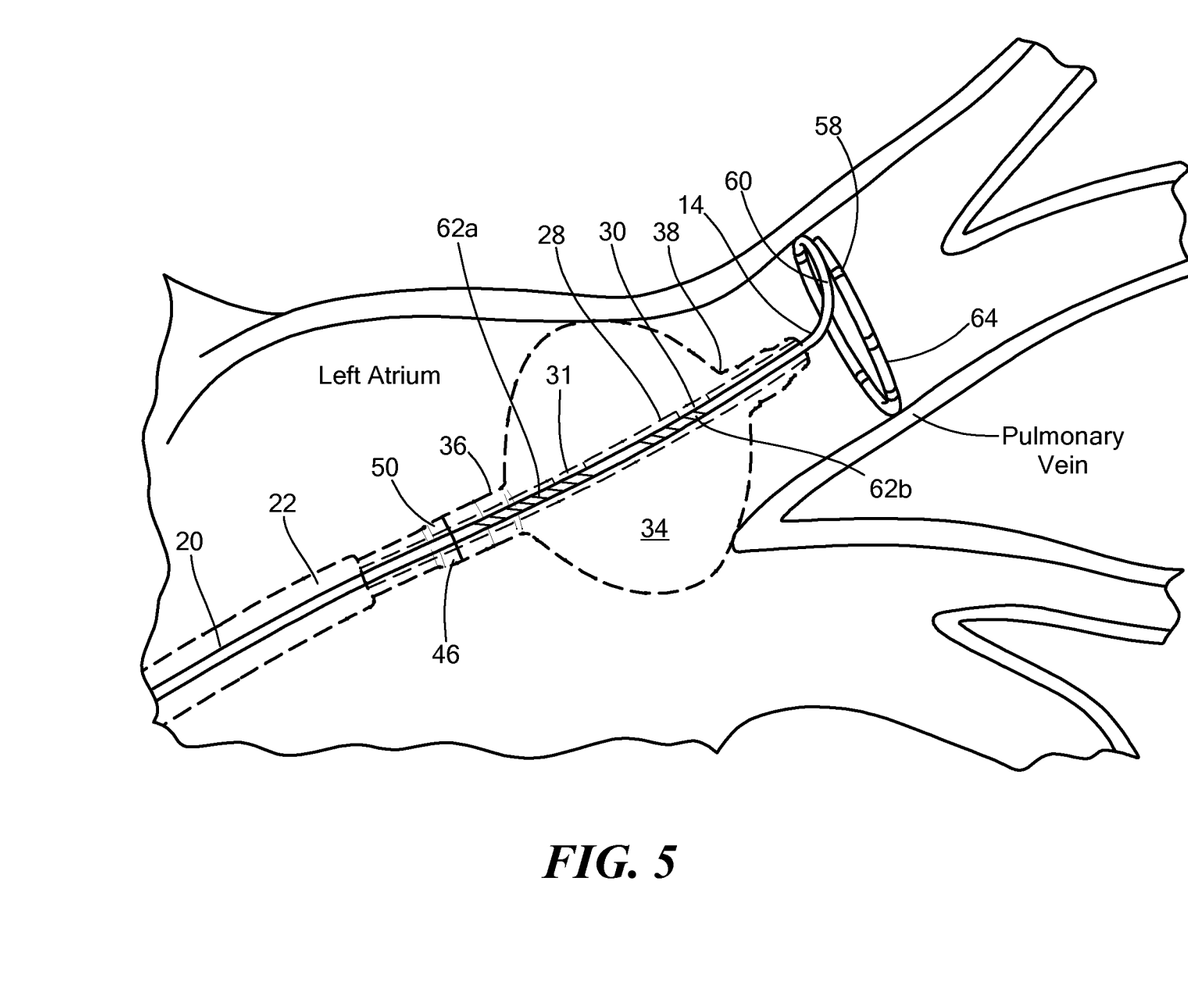
FIG. 5 shows an alternate view of the heatable mapping catheter within the exemplary cryotreatment catheter in the configuration of FIG. 4.

As shown in FIGS. 3 and 5, the mapping catheter 14 may include a plurality of heating elements 62 located on the mapping catheter 14 such that one or more heating elements are disposed within the guide wire lumen 28 proximate the cryoballoon 34 (that is, within the area of the guide wire lumen 28 most affected by the temperature of the cryoballoon 34) when the mapping catheter is extended (FIGS. 2 and 3) and when the mapping catheter 14 is retracted (FIGS. 4 and 5). For example, FIG. 3 shows a first set of heating elements 62a that is disposed within the cryoballoon 34 when the mapping catheter 14 is extended, and a second set of heating elements 62b that may be disposed within the cryoballoon 34 when the mapping catheter 14 is retracted. Depending on the position of the mapping catheter 14, either the first set 62a, second set 62b, or both sets of heating elements may selectively be activated. Further, an individual heating element 62 from either set may selectively be activated alone or in combination with other heating elements 62. As non-limiting examples, the one or more heating elements 62 may be electrodes to which radiofrequency energy is delivered, such as electrode bands (as shown in FIG. 3), or the one or more heating elements 62 may be flexible heating films or wires that can be wrapped around the mapping catheter 14 (as shown in FIG. 5). For example, the one or more heating elements 62 may be disposed on an outer surface of the mapping catheter 14 if they are composed of biocompatible materials (for example, if the one or more heating elements 62 are composed of metal such as platinum-iridium alloy, gold, or gold plated metals such as copper or stainless steel), or the one or more heating elements 62 be disposed or incorporated within the mapping catheter 14 if they are conductive and/or not biocompatible.

The one or more processors 70 may be in communication with the one or more temperature 30 and/or pressure 31 sensors, and programmable to activate the one or more heating elements 62 automatically when temperature signals sent from one or more temperature sensors 30 to the computer 66 indicate that freezing temperatures have been reached within the guide wire lumen 28 or are about to be reached. As a non-limiting example, one or more temperature sensors 30 may be positioned inside the guide wire lumen 28 (as shown in FIG. 3), inside the cryoballoon 34, such as in the proximal portion of the balloon, outside the cryoballoon, such as at the tissue-balloon interface, or within or on the distal portion 60 of the mapping catheter 14. For example, the one or more processors 70 may activate the one or more heating elements 62 when the temperature within the guide wire lumen is between approximately 0° C. and approximately −10° C., as sensed by one or more temperature sensors 30, such as those located within the guide wire lumen 28. Additionally or alternatively, the one or more processors 70 may activate the one or more heating elements 62 when one or more pressure sensors 31 indicate that liquid inside the guide wire lumen 28 has frozen (for example, if using the pressure wedge monitoring technique, disappearance of the pressure wave may indicate frozen fluid). As a non-limiting example, a pressure sensor 31 may be located on the mapping catheter 14 at a location on the mapping catheter 14 that would be within the guide wire lumen 28 at the onset of cryotreatment. FIG. 3 shows a pressure sensor 31 in such a location on the mapping catheter 14 having no heating elements. If the pressure sensor 31 is located on a mapping catheter 14 with heating elements, the pressure sensor 31 could be located, for example, proximal of one or more heating elements 62. At this location, the pressure sensor 31 may be able to sense the disappearance of pressure waves, which is an indicator of frozen liquid within the guide wire lumen 28. Additionally or alternatively, the one or more heating elements 62 may be manually activated based on, for example, temperature signals from the one or more temperature sensors 30 or time from initiation of cryotreatment. Whether activated manually or automatically, only the one or more heating elements 62 located within the guide wire lumen 28 proximate the cryoballoon 34 (that is, within the area of the guide wire lumen 28 most affected by the temperature of the cryoballoon 34) may be activated. Further, the portion of the guide wire lumen 28 proximate the cryoballoon may include an insulative layer 63 so that the heat generated by the one or more heating elements 62 will only affect the temperature of fluid within the guide wire lumen 28, with the warming effect within the guide wire lumen 28 being faster and more efficient, but will not affect the temperature of coolant circulating through the cryoballoon 34 and/or the temperature of the cryoballoon 34 itself.

Figure 6:
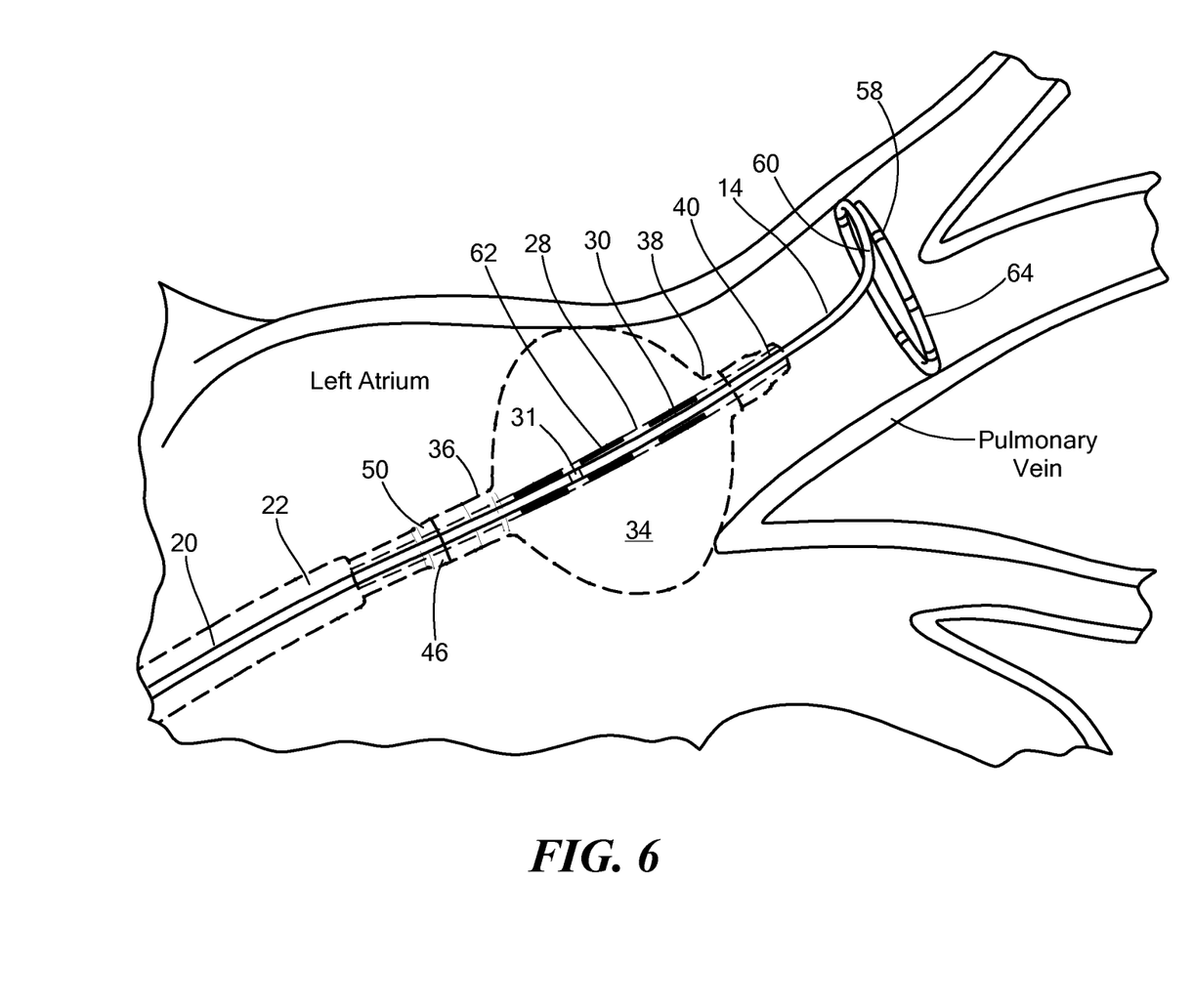
FIG. 6 shows a cryotreatment cryotreatment catheter having one or more heating elements within the guide wire lumen.

Referring now to FIG. 6, an alternative embodiment of a cryotreatment catheter is shown. As shown in FIG. 6, the cryotreatment catheter 12 may include one or more heating elements 62 disposed within the guide wire lumen 28 proximate the cryoballoon 34 (that is, in the area of the guide wire lumen 28 most affected by the temperature of the cryoballoon 34). Although six heating elements 62 are shown in FIG. 6, it will be understood that any number and/or configuration of heating elements 62 may be used. For example, the one or more heating elements 62 may be discrete, continuous, elongate, wound about an inner surface of the guide wire lumen 28, or the like. The one or more heating elements 62 may be electrodes (for example, radiofrequency electrodes), bands or areas of exposed conductive material, and/or conductive wires or braids affixed to an inner surface of the lumen and/or integrated within the guide wire lumen 28. In such an embodiment, the mapping catheter 14 may be without heating elements 62. Thus, fluid within the guide wire lumen 28 may be thawed or prevented from freezing by the one or more heating elements 62 regardless of the position of the mapping catheter 14 (that is, whether the mapping catheter 14 is extended, retracted, or in a position therebetween). It will be understood that one or more heating elements 62 may be included both on an inner surface of the guide wire lumen 28 (as shown in FIG. 6) and on the mapping catheter 14 (as shown in FIGS. 3 and 5). Such a configuration would enhance the heating potential and accelerate the melting process.

Figure 7:
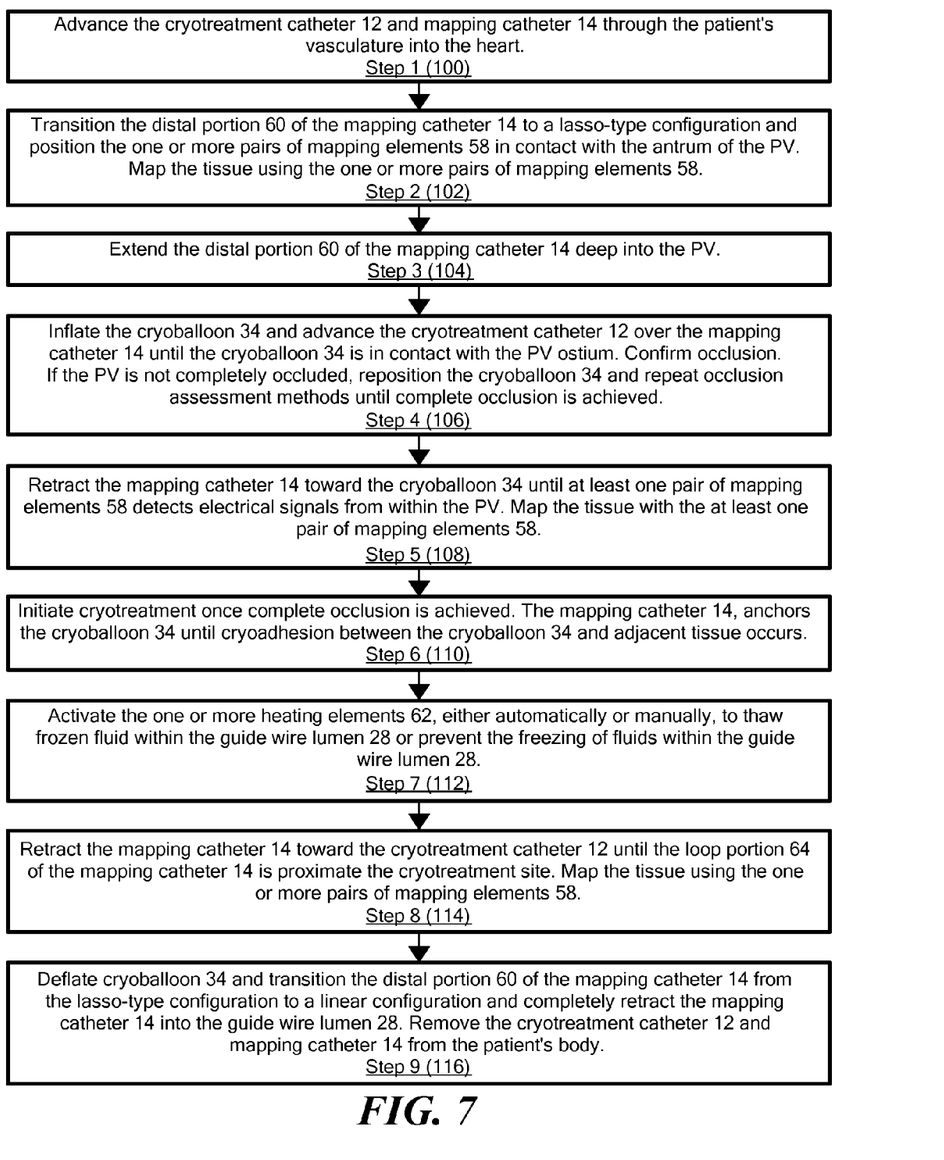
FIG. 7 shows a method of treating tissue using a cryotreatment system with one or more heating elements.

Referring now to FIG. 7, a method of treating tissue using a cryotreatment system with one or more heating elements is shown. In the first step 100 of the method, the cryotreatment catheter 12 and mapping catheter 14 may be advanced through the patient's vasculature into the heart (for example, the left atrium of the heart). In the second step 102 of the method, the distal portion 60 of the mapping catheter 14 may be transitioned to a lasso-type configuration and positioned such that at least one of the one or more pairs of mapping elements 58 are in contact with the PV antrum. Electrical signals in the tissue may be detected and recorded (that is, the tissue may be mapped), such as PV potentials. In the third step 104 of the method, the mapping catheter 14 may be advanced deep within a PV (referred to as being in the extended position). In this position, the mapping catheter 14 may anchor the cryotreatment device 12. For example, the distal portion 60 of the mapping catheter 14, the area on which the one or more pairs of mapping elements 58 may be disposed, may be manipulated and/or steered to assume a lasso-type configuration, such that the loop portion 64 is in contact with at least a portion of an inner circumference of the PV. Even though the one or more pairs of mapping elements 58 may be in contact with the PV tissue, electrical signals may be absent and, therefore, no recording may be performed in this step.

In the fourth step 106 of the method, the cryoballoon 34 may be inflated and the cryotreatment catheter 14 advanced over the mapping catheter 14 until the cryoballoon 34 is in contact with the PV ostium. Contrast medium with fluoroscopy and/or other methods such as pressure wedge monitoring may be used to confirm occlusion. If these methods indicate that the PV is not completely occluded, the cryoballoon 34 may be repositioned and the assessment methods repeated until complete occlusion is achieved. In the fifth step 108 of the method, the mapping catheter 14 may be partially retracted toward the cryoballoon 34 until at least one pair of mapping elements 58 detects electrical signals from within the PV. This position may also be referred to as an extended position, although the mapping catheter 14 is not extended as far within the PV as in the second step 102 of the method. Once electrical signals are detected, they may be recorded by the one or more pairs of mapping elements 58. If this retraction of the mapping catheter 14 causes the cryoballoon 34 to slip from the ostium and complete occlusion is lost, the mapping catheter 14 may be re-extended to position the distal portion 60 deeper within the PV. At this location, electrical signals may be lost (that is, not be present). However, it will be understood that this fifth step is optional. Rather, the distal portion 60 of the mapping catheter 14 may remain deep within the PV until after cryoadhesion occurs and the anchoring function of the mapping catheter 14 is less important. The mapping catheter 14 may be extended or retracted at any stage of cryotreatment because of the heat generated by the one or more heating elements 62.

In the sixth step 110 of the method, cryotreatment may be initiated once complete occlusion is achieved. For example, coolant may be circulated from the fluid supply reservoir 48 through the fluid flow paths of the system in order to cool the cryoballoon 34. In one embodiment, unexpanded coolant may pass from the fluid supply reservoir 48 through the fluid injection lumen 46 and into the cryoballoon 34. Although not shown, fluid may pass from the fluid injection lumen 46 into the cryoballoon 34 through a fluid injection element such as a nozzle, opening, or other component. After exiting the fluid injection element, the unexpanded coolant may expand and cool the cryoballoon 34 by the Joule-Thomson effect. Expanded coolant may then pass into the fluid recovery lumen 50 and either vented to the atmosphere, stored in the fluid recovery reservoir 52, or recirculated through the system 10. Fluid may be drawn into the fluid recovery lumen 50 from the cryoballoon 34 by a vacuum 54. The mapping catheter 14 may be left in the extended position during initiation of cryotreatment and used to anchor or otherwise offer support to the cryoballoon 34 until cryoadhesion between the cryoballoon 34 and adjacent tissue occurs.

In the seventh step 112 of the method, the one or more heating elements 62 may be activated, either automatically or manually. For example, readings from one or more sensors 30, such as temperature sensors and/or pressure sensors, may cause the one or more processors 70 to activate the one or more heating elements 62 automatically. Additionally or alternatively, readings from the one or more sensors 30, such as temperature or pressure measurements, may be shown on the display 68. The time elapsed since initiation of cryotreatment may also be displayed. Based on the displayed measurements, the user may activate one or more heating elements 62 either individually or in groups. As a non-limiting example, the heating elements 62 may be activated, either automatically or manually, when the temperature within the cryoballoon 34 or the guide wire lumen 28 reaches a threshold temperature (for example, when the temperature within the guide wire lumen 28 is approximately 0° C.±5° C. or at 10 seconds±5 seconds after commencement of cryotreatment.

In the eighth step 114 of the method, the mapping catheter 14 may be retracted toward the cryotreatment catheter 12 until the loop portion 64 of the mapping catheter 14 is proximate the cryotreatment site (but outside the guide wire lumen 28). It will be understood that the mapping catheter 14 may be retracted or extended by any amount in order to detect and record an additional set of PV potentials, and does not have to be retracted all the way to the cryotreatment site. Due to the warming effect of activation of the one or more heating elements 62, the mapping catheter 14 may be longitudinally movable in either direction in order to record additional electrical signals. Further, the sixth step 110 of the method may be repeated as many times as desired. Indeed, any of the method steps may be repeated as many times as is necessary to seat the cryoballoon 34 against the PV ostium, acquire adequate mapping data, and/or securely anchor the mapping catheter 14 and cryotreatment catheter 12 in position. As an example, following cryotreatment, the distal portion 60 of the mapping catheter 14 may be withdrawn from the PV and repositioned at the PV antrum (for example, the distal portion 60 may be in the lasso-type configuration and at least partially encircle the PV ostium) such that at least one pair of mapping elements 58 detects and records electrical signals from the PV antrum. This may allow for assessment of the effectiveness of the cryotreatment. Depending at least in part on the signals detected and recorded from the PV antrum, the cryotreatment device 12 may be used to retreat the same area of tissue or may be relocated to treat a different area of tissue. Cardiac issue, such as the PV antrum, may be mapped as many times and in as many locations as necessary to confirm that the cryotreatment was successful.

In the ninth step 116 of the method, the cryoballoon 34 may be deflated and the distal portion 60 of the mapping catheter 14 may be transitioned from the lasso-type configuration to a linear configuration and completely retracted within the guide wire lumen 28. For example, the ninth step 116 may be performed once mapping has confirmed successful cryotreatment. The cryotreatment catheter 12, with the mapping catheter 14 therein, may then be removed from the patient's body. Alternatively, the mapping catheter 14 may be completely removed from the cryotreatment catheter 12 before the cryotreatment catheter 12 is removed from the patient's body.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:
1. A cryotreatment system comprising:
  a cryotreatment catheter including:
    a first elongate body having a longitudinal axis;
    a lumen disposed within the first elongate body along the longitudinal axis; and
    a cryoballoon coupled to a distal portion of the first elongate body, at least a portion of the lumen being disposed within the cryoballoon; and a mapping catheter including:
- a second elongate body being disposable within the lumen and movable along the longitudinal axis; and
- at least two heatable regions on the second elongate body, at least one of the at least two heatable regions being configured to be disposed within the lumen within the cryoballoon when the mapping catheter is extended a first distance beyond the first elongate body, and at least one other of the at least two heatable regions being disposed within the lumen within the cryoballoon when the mapping catheter is extended a second distance beyond the first elongate body, the at least two heatable regions being configured to be activated independently of each other.

2. The system of claim 1, further comprising a console including a computer having a processor, wherein the processor is in communication with at least one of the cryotreatment catheter and the mapping catheter.

3. The system of claim 2, further comprising at least one of a temperature sensor and a pressure sensor, wherein the at least one of the temperature sensor and the pressure sensor is in communication with the processor.

4. The system of claim 3, wherein the processor is programmable to activate at least one of the at least two heatable regions when the temperature sensor indicates the lumen of the cryotreatment catheter has reached a threshold temperature.

5. The system of claim 4, wherein the threshold temperature is approximately 0° C.

6. The system of claim 1, wherein at least one of the at least two heatable regions includes a band electrode.

7. The system of claim 1, wherein at least one of the at least two heatable regions includes a thermally conductive wire wound about at least a portion of the second elongate body.

8. The system of claim 1, the system further comprising a radiofrequency energy source in electrical communication with the at least two heatable regions.

9. The system of claim 1, wherein at least one of the at least two heatable regions is disposed within the lumen proximate the cryoballoon, and is configured to be activated to generate heat during at least a portion of a time during which the cryoballoon is activated.

* * * * *